United States Patent
Folan et al.

(10) Patent No.: US 11,351,045 B2
(45) Date of Patent: *Jun. 7, 2022

(54) STENT ANCHORING SYSTEM

(71) Applicant: BOSTON SCIENTIFIC SCIMED, INC., Maple Grove, MN (US)

(72) Inventors: Martyn G. Folan, Galway (IE); Martin Hynes, Galway (IE); Damien V. Nolan, Galway (IE); Enda Connaughton, Galway (IE); Matthew Montague, Galway (IE); Thomas M. Keating, Galway (IE); Michael Walsh, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 136 days.

This patent is subject to a terminal disclaimer.

(21) Appl. No.: 16/803,470

(22) Filed: Feb. 27, 2020

(65) Prior Publication Data

US 2020/0197197 A1     Jun. 25, 2020

Related U.S. Application Data

(63) Continuation of application No. 15/807,549, filed on Nov. 8, 2017, now Pat. No. 10,603,193.
(Continued)

(51) Int. Cl.
    *A61F 2/04*          (2013.01)
    *A61F 2/848*        (2013.01)
    (Continued)

(52) U.S. Cl.
    CPC ................ *A61F 2/848* (2013.01); *A61F 2/04* (2013.01); *A61F 2/88* (2013.01); *A61F 2/90* (2013.01);
    (Continued)

(58) Field of Classification Search
    CPC .... A61F 2/848; A61F 2/04; A61F 2/88; A61F 2/90; A61F 2002/8483; A61F 2220/0016; A61F 2210/0014; A61F 2230/0069
    See application file for complete search history.

(56) References Cited

U.S. PATENT DOCUMENTS 5,167,614 A    12/1992   Tessman et al.
5,397,355 A    3/1995   Marin et al.
(Continued)

FOREIGN PATENT DOCUMENTS

EP          1923020 A2    5/2008
WO     2009042789 A2    4/2009
(Continued)

OTHER PUBLICATIONS

International Search Report and Written Opinion, International Application No. PCT/US2017/060728, dated Feb. 13, 2018 (11 pages).

*Primary Examiner* — Paul B Prebilic
(74) *Attorney, Agent, or Firm* — Seager, Tufte & Wickhem, LLP

(57) ABSTRACT

An illustrative stent may comprise an elongated tubular member having a first end and a second end and an intermediate region disposed therebetween. The elongated tubular member may include at least one barb attached thereto. The barb may be configured to be tucked under a filament of the stent during delivery of the stent and protrude radially from the stent, when the stent is deployed.

20 Claims, 13 Drawing Sheets

Related U.S. Application Data

(60) Provisional application No. 62/419,810, filed on Nov. 9, 2016.

(51) Int. Cl.
*A61F 2/88* (2006.01)
*A61F 2/90* (2013.01)

(52) U.S. Cl.
CPC ............. *A61F 2002/8483* (2013.01); *A61F 2230/0069* (2013.01)

(56) References Cited

U.S. PATENT DOCUMENTS

| | | | |
|---|---|---|---|
| 5,591,197 | A | 1/1997 | Orth et al. |
| 5,800,526 | A | 9/1998 | Anderson et al. |
| 6,911,042 | B2 | 6/2005 | Weadock |
| 7,081,132 | B2 | 7/2006 | Cook et al. |
| 7,147,661 | B2 | 12/2006 | Chobotov et al. |
| 7,223,284 | B2 | 5/2007 | Khosravi et al. |
| 7,608,114 | B2 | 10/2009 | Levine et al. |
| 7,655,034 | B2 | 2/2010 | Mitchell et al. |
| 7,867,267 | B2 | 1/2011 | Sullivan et al. |
| 7,905,915 | B2 * | 3/2011 | Young ............... A61F 2/90 623/1.36 |
| 7,914,568 | B2 | 3/2011 | Cully et al. |
| 8,137,301 | B2 | 3/2012 | Levine et al. |
| 8,162,871 | B2 | 4/2012 | Levine et al. |
| 8,292,946 | B2 | 10/2012 | Thistle et al. |
| 8,298,281 | B2 | 10/2012 | Majercak et al. |
| 8,343,204 | B2 | 1/2013 | Osborne |
| 8,348,988 | B2 | 1/2013 | Lad et al. |
| 8,372,141 | B2 | 2/2013 | Majercak et al. |
| 8,372,142 | B2 | 2/2013 | Majercak et al. |
| 8,372,143 | B2 | 2/2013 | Majercak et al. |
| 8,394,139 | B2 | 3/2013 | Roeder et al. |
| 8,444,688 | B2 | 5/2013 | Sherry |
| 8,696,739 | B2 | 4/2014 | Dierking et al. |
| 8,702,785 | B2 | 4/2014 | Khan et al. |
| 8,715,334 | B2 | 5/2014 | Clerc et al. |
| 8,747,457 | B2 | 6/2014 | Petersen |
| 8,821,565 | B2 | 9/2014 | Demetriades et al. |
| 8,858,617 | B2 | 10/2014 | Roeder et al. |
| 8,864,813 | B2 | 10/2014 | Barr |
| 9,089,445 | B2 | 7/2015 | Agnew et al. |
| 9,192,466 | B2 | 11/2015 | Kovalsky et al. |
| 9,237,959 | B2 | 1/2016 | Cage |
| 9,254,204 | B2 | 2/2016 | Roeder et al. |
| 9,278,018 | B2 | 3/2016 | Roeder |
| 9,339,378 | B2 | 5/2016 | Quadri et al. |
| 2002/0032481 | A1 | 3/2002 | Gabbay |
| 2003/0114919 | A1 | 6/2003 | McQuiston et al. |
| 2003/0220683 | A1 | 11/2003 | Minasian et al. |
| 2004/0117004 | A1 | 6/2004 | Osborne et al. |
| 2004/0267348 | A1 | 12/2004 | Gunderson et al. |
| 2005/0033398 | A1 | 2/2005 | Seguin |
| 2006/0161265 | A1 | 7/2006 | Levine et al. |
| 2007/0027526 | A1 | 2/2007 | Demetriades et al. |
| 2009/0048664 | A1 | 2/2009 | Cage |
| 2009/0082847 | A1 | 3/2009 | Zacharias et al. |
| 2009/0240340 | A1 | 9/2009 | Levine et al. |
| 2009/0248171 | A1 | 10/2009 | Levine et al. |
| 2009/0270967 | A1 | 10/2009 | Fleming, III et al. |
| 2012/0065723 | A1 | 3/2012 | Drasler et al. |
| 2012/0130470 | A1 | 5/2012 | Agnew et al. |
| 2012/0232637 | A1 | 9/2012 | Demetriades et al. |
| 2013/0018452 | A1 | 1/2013 | Weitzner et al. |
| 2013/0144375 | A1 | 6/2013 | Giasolli et al. |
| 2013/0172983 | A1 | 7/2013 | Clerc et al. |
| 2013/0245749 | A1 | 9/2013 | Sherry |
| 2014/0046366 | A1 | 2/2014 | O'Hara et al. |
| 2014/0067038 | A1 | 3/2014 | Daugherty et al. |
| 2014/0081416 | A1 | 3/2014 | Clerc et al. |
| 2014/0214150 | A1 | 7/2014 | Clerc et al. |
| 2014/0277442 | A1 | 9/2014 | Seddon et al. |
| 2015/0119974 | A1 | 4/2015 | Rothstein |
| 2015/0245931 | A1 | 9/2015 | Eaton |
| 2016/0058544 | A1 | 3/2016 | Levine et al. |
| 2016/0095725 | A1 | 4/2016 | Roeder et al. |
| 2016/0242940 | A1 | 8/2016 | Krautkremer et al. |

FOREIGN PATENT DOCUMENTS

| | | |
|---|---|---|
| WO | 2013171730 A1 | 11/2013 |
| WO | 2014025959 A1 | 2/2014 |
| WO | 2014025959 A9 | 5/2014 |

* cited by examiner

STENT ANCHORING SYSTEM

CROSS-REFERENCE TO RELATED APPLICATIONS

This application is a continuation of U.S. patent application Ser. No. 15/807,549, filed Nov. 8, 2017, now U.S. Pat. No. 10,603,193, which claims priority under 35 U.S.C. § 119 to U.S. Provisional Application Ser. No. 62/419,810, filed Nov. 9, 2016, the entirety of which is incorporated herein by reference.

TECHNICAL FIELD

The present disclosure pertains to medical devices, methods for manufacturing medical devices, and uses thereof. More particularly, the present disclosure pertains to an anti-migration stent for implantation in a body lumen, and associated methods.

BACKGROUND

Implantable stents are devices that are placed in a body lumen, such as the esophageal tract, the gastrointestinal tract (including the intestine, stomach and the colon), tracheobronchial tract, urinary tract, biliary tract, vascular system, etc. to provide support and to maintain the body lumen open. These stents are manufactured by any one of a variety of different manufacturing methods and may be used according to any one of a variety of methods. Of the known stents, delivery systems, and methods, each has certain advantages and disadvantages. For example, in some stents, the compressible and flexible properties that assist in stent delivery may also result in a stent that has a tendency to migrate from its originally deployed position. For example, stents that are designed to be positioned in the esophageal or gastrointestinal tract may have a tendency to migrate due to peristalsis (i.e., the involuntary constriction and relaxation of the muscles of the esophagus, intestine, and colon which push the contents of the canal therethrough). Thus, there is an ongoing need to provide alternative stents having anti-migration features and associated delivery systems as well as alternative methods for manufacturing and using stents having anti-migration features and associated delivery systems.

BRIEF SUMMARY

This disclosure provides design, material, manufacturing method, and use alternatives for medical devices. An example medical device may include a stent.

One illustrative example is a stent including an elongated tubular member comprising at least one interwoven filament defining a plurality of cells. The elongated tubular member is configured to move between a collapsed configuration and an expanded configuration. In the collapsed configuration, the plurality of cells have a first profile and in the expanded configuration the plurality of cells have a second profile different from the first profile. The stent also includes at least one barb attached to the at least one filament at one end of the barb and extending towards a free end. The free end of the at least one barb is configured to be positioned radially inward to an adjacent winding of the at least one interwoven filament when the elongated tubular member is in the collapsed configuration and to extend radially outward from the elongated tubular member when the elongated tubular member is in the expanded configuration.

Additionally or alternatively to any example above, the first profile of the plurality of cells has a major dimension extending along a longitudinal axis of the elongated tubular member.

Additionally or alternatively to any example above, the second profile of the plurality of cells has a major dimension extending along a circumference of the elongated tubular member.

Additionally or alternatively to any example above, the at least one barb comprises a wire.

Additionally or alternatively to any example above, the at least one barb is attached to the at least one filament at a terminal end of the at least one barb.

Additionally or alternatively to any example above, the at least one barb is attached to the at least one filament along a length of the at least one barb, the length extending from a terminal end to a point proximal to the free end.

Additionally or alternatively to any example above, the at least one barb is attached to the at least one filament at a first end of the at least one barb and a second end of the at least one barb, wherein the free end of the at least one barb is a region intermediate to the first end and the second end.

Additionally or alternatively to any example above, the at least one barb has a generally triangular shape.

Additionally or alternatively to any example above, the at least one barb comprises a wire helically wound around the at least one filament.

Additionally or alternatively to any example above, the at least one barb is biased to extend radially outward from the elongated tubular member when unconstrained.

Additionally or alternatively to any example above, the at least one barb comprises a material combination which behaves like a temperature sensitive bimetallic strip.

Additionally or alternatively to any example above, the at least one barb comprises a plurality of barbs spaced along a length and a circumference of the elongated tubular member.

Additionally or alternatively to any example above, the at least one barb comprises a plurality of barbs, wherein at least some of the plurality of barbs have a first length and at least some of the plurality of barbs have a second length different from the first length.

Additionally or alternatively to any example above, the at least one barb comprises two or more wires fixed at a same location on the at least one filament.

Additionally or alternatively to any example above, when in the collapsed configuration the adjacent winding is configured to exert a radially inward force on the at least one barb.

Another example is a stent including an elongated tubular member comprising at least one filament wound to form a plurality of cells. The elongated tubular member is configured to move between a collapsed configuration and an expanded configuration. The stent also includes a plurality of barbs affixed to the at least one filament and comprising a shape memory wire. The plurality of barbs are biased to extend radially outward from the elongated tubular member when unconstrained. In the collapsed configuration, the at least one filament applies a radially inward constraining force to a free end of each barb of the plurality of barbs such that the free ends are constrained radially inward of the at least one filament, and as the elongated tubular member moves from the collapsed configuration to the expanded configuration the free end of at least some of the plurality of barbs is unconstrained by the at least one filament and extends radially outward from the elongated tubular member.

Additionally or alternatively to any example above, at least some of the plurality of barbs have a first length and at least some of the plurality of barbs have a second length greater than the first length.

Additionally or alternatively to any example above, the constraining force is removed from the barbs having the first length before the barbs having the second length.

Yet another example is a stent including an elongated tubular member comprising at least one filament wound to form a plurality of cells. The elongated tubular member is configured to move between a collapsed configuration and an expanded configuration. In the collapsed configuration, the plurality of cells have a first profile and in the expanded configuration the plurality of cells have a second profile different from the first profile. The stent also includes at least one barb attached to the at least one filament at one end of the barb and extending towards a free end. The first profile is configured to exert a constraining force on the at least one barb to position the at least one barb radially inward of the at least one filament and the second profile is configured to remove the constraining force from the at least one barb such that the free end of the at least one barb extends radially outward from the elongated tubular member.

Additionally or alternatively to any example above, the at least one barb comprises a shape memory material.

Additionally or alternatively to any example above, when the free end of the at least one barb extends radially outward from the elongated tubular member, the at least one barb is at an angle of in the range of 2° to 90° relative to a longitudinal axis of the elongated tubular member.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The invention may be more completely understood in consideration of the following detailed description of various embodiments in connection with the accompanying drawings, in which.

Figure 1:
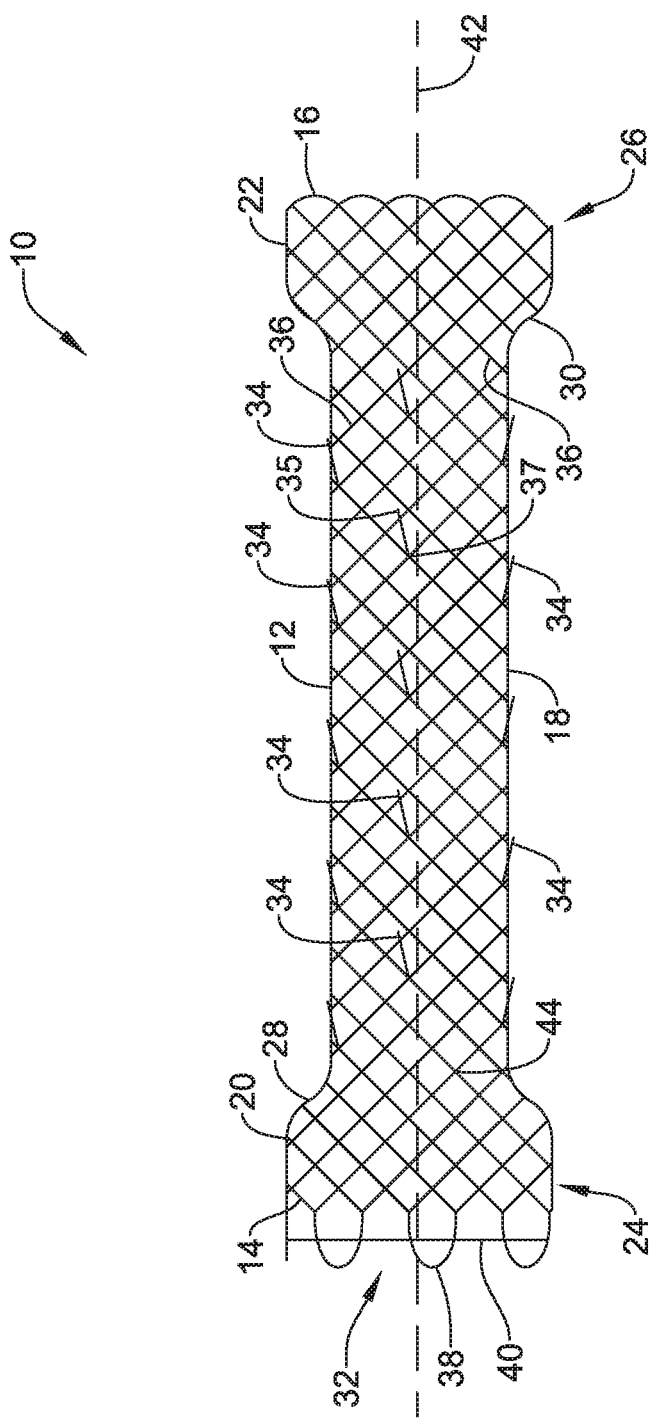
FIG. 1 is a side view of an illustrative stent having an anti-migration anchoring system.

While the disclosure is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

In some instances, it may be desirable to provide an endoluminal implant, or stent, that can deliver luminal patency in a patient with an esophageal stricture or other medical condition. Such stents may be used in patients experiencing dysphagia, sometimes due to esophageal cancer. An esophageal stent may allow a patient to maintain nutrition via oral intake during cancer treatment or palliation periods. However, a common complication of gastrointestinal (GI) stents is stent migration due to the peristaltic motion subjected to the stent. It may be desirable to provide a stent that can deliver luminal patency while minimizing migration of the stent. While the embodiments disclosed herein are discussed with reference to esophageal stents, it is contemplated that the stents described herein may be used and sized for use in other locations such as, but not limited to: bodily tissue, bodily organs, vascular lumens, non-vascular lumens and combinations thereof, such as, but not limited to, in the coronary or peripheral vasculature, trachea, bronchi, colon, small intestine, biliary tract, urinary tract, prostate, brain, stomach and the like.

FIG. 1 illustrates a side view of an illustrative endoluminal implant 10, such as, but not limited to, a stent. In some instances, the stent 10 may be formed from an elongated tubular member 12. While the stent 10 is described as generally tubular, it is contemplated that the stent 10 may take any cross-sectional shape desired. The stent 10 may have a first, or proximal end 14, a second, or distal end 16, and an intermediate region 18 disposed between the first end 14 and the second end 16. The stent 10 may include a lumen 32 extending from a first opening adjacent the first end 14 to a second opening adjacent to the second end 16 to allow for the passage of food, fluids, etc.

The stent 10 may be expandable from a first radially collapsed configuration (not explicitly shown) to a second radially expanded configuration. In some cases, the stent 10 may be deployed to a configuration between the collapsed configuration and a fully expanded configuration. The stent 10 may be structured to extend across a stricture and to apply a radially outward pressure to the stricture in a lumen to open the lumen and allow for the passage of foods, fluids, air, etc.

The proximal end 14 of the stent 10 may include a plurality of loops 38. The loops 38 may be configured to receive a retrieval tether or suture 40 interwoven therethrough, or otherwise passing through one or more of the loops 38. The retrieval suture 40 may be used to collapse and retrieve the stent 10, if so desired. For example, the retrieval suture 40 may be pulled like a drawstring to radially collapse the proximal end 14 of the stent 10 to facilitate removal of the stent 10 from a body lumen.

The stent 10 may have a woven structure, fabricated from a number of filaments or struts 36. In some embodiments, the stent 10 may be knitted or braided with a single filament interwoven with itself and defining open cells. In other embodiments, the stent 10 may be braided with several filaments interwoven together and define open cells. Some exemplary stents including braided filaments include the WallFlex®, WALLSTENT®, and Polyflex® stents, made and distributed by Boston Scientific, Corporation. In another embodiment, the stent 10 may be knitted, such as the Ultraflex™ stents made by Boston Scientific, Corporation. In yet another embodiment, the stent 10 may be of a knotted type, such the Precision Colonic™ stents made by Boston Scientific, Corporation. In still another embodiment, the stent 10 may be a laser cut tubular member, such as the EPIC™ stents made by Boston Scientific, Corporation. A laser cut tubular member may have an open and/or closed cell geometry including one or more interconnected filaments or struts defining open cells therebetween. In some instances, an inner and/or outer surface of the stent 10 may be entirely, substantially or partially, covered with a polymeric covering or coating. The covering or coating may extend across and/or occlude one or more, or a plurality of the cells defined by the struts or filaments 36. The covering or coating may help reduce food impaction and/or tumor or tissue ingrowth. In some cases, the stent 10 may be a self-expanding stent (SES), although this is not required.

In some instances, in the radially expanded configuration, the stent 10 may include a first end region 20 proximate the proximal end 14 and a second end region 22 proximate the second end 16. In some embodiments, the first end region 20 and the second end region 22 may include retention features or anti-migration flared regions 24, 26 having enlarged diameters relative to the intermediate portion 18. The anti-migration flared regions 24, 26, which may be positioned adjacent to the first end 14 and the second end 16 of the stent 10, may be configured to engage an interior portion of the walls of the esophagus or other body lumen. In some embodiments, the retention features, or flared regions 24, 26 may have a larger diameter than the cylindrical intermediate region 18 of the stent 10 to prevent the stent 10 from migrating once placed in the esophagus or other body lumen. It is contemplated that the transition 28, 30 from the cross-sectional area of the intermediate region 18 to the retention features or flared regions 24, 26 may be gradual, sloped, or occur in an abrupt step-wise manner, as desired.

In some embodiments, the first anti-migration flared region 24 may have a first outer diameter and the second anti-migration flared region 26 may have a second outer diameter. In some instances, the first and second outer diameters may be approximately the same, while in other instances, the first and second outer diameters may be different. In some embodiments, the stent 10 may include only one or none of the anti-migration flared regions 24, 26. For example, the first end region 20 may include an anti-migration flare 24 while the second end region 22 may have an outer diameter similar to the intermediate region 18. It is further contemplated that the second end region 22 may include an anti-migration flare 26 while the first end region 20 may have an outer diameter similar to an outer diameter of the intermediate region 18. In some embodiments, the stent 10 may have a uniform outer diameter from the first end 14 to the second end 16. In some embodiments, the outer diameter of the intermediate region 18 may be in the range of 15 to 25 millimeters. The outer diameter of the anti-migration flares 24, 26 may be in the range of 20 to 30 millimeters. It is contemplated that the outer diameter of the stent 10 may be varied to suit the desired application.

It is contemplated that the stent 10 can be made from a number of different materials such as, but not limited to, metals, metal alloys, shape memory alloys and/or polymers, as desired, enabling the stent 10 to be expanded into shape when accurately positioned within the body. In some instances, the material may be selected to enable the stent 10 to be removed with relative ease as well. For example, the stent 10 can be formed from alloys such as, but not limited to, nitinol and Elgiloy®. Depending the on material selected for construction, the stent 10 may be self-expanding or require an external force to expand the stent 10. In some embodiments, composite filaments may be used to make the stent 10, which may include, for example, an outer shell or cladding made of nitinol and a core formed of platinum or other radiopaque material. It is further contemplated the stent 10 may be formed from polymers including, but not limited to, polyethylene terephthalate (PET). In some instances, the filaments of the stent 10, or portions thereof, may be bioabsorbable or biodegradable, while in other instances the filaments of the stent 10, or portions thereof, may be biostable.

The stent 10 may further include one or more anti-migration or retention features, such as barbs 34 (e.g., tines, quills, etc.) attached to one or more of the filaments 36. The barbs 34 may be configured to extend radially outward from an outer surface (and/or a longitudinal axis 42) of the stent body 12 to engage bodily tissue. In some cases, the barbs 34 may be filament-like or wire-like structures. It is contemplated that a single wire or a group (e.g., two or more) of wires may form a barb 34. In some cases, the barbs 34 may comprise a plate-like structure. In some instances, the barbs 34 may be a unitary portion of the filaments. The barbs 34 may have a pointed or tapered free end to facilitate engagement into the tissue. The stent 10 may include any number of barbs 34 desired such as, but not limited to, one or more, five or more, 20 or more, 50 or more, 100 or more, etc.

The barbs 34 may be biased to extend radially outward from the longitudinal axis 42 of the stent 10, when the stent 10 is in the expanded configuration and the barbs 34 are unconstrained. For example, when the stent 10 is delivered at the desired location, the barbs 34 may extend out from the filaments 36 (e.g., away from the longitudinal axis 42 of the stent 10) at a desired angle and interact with (e.g., penetrate) the surrounding anatomy to anchor the stent 10 and aid in anti-migration of the stent 10. It is contemplated that the angle of the barbs 34 relative to the longitudinal axis 42 may be in the range of 2° (e.g., generally parallel to the longitudinal axis 42) to 90° (e.g., generally orthogonal to the longitudinal axis 42). In some cases, the free end 35 of the barbs 34 may angle towards the distal end 16 of the stent 10. In other cases, the barbs 34 may angle towards the proximal end 14 of the stent 10. It is further contemplated that on the same stent 10, the free end 35 of one or more of the barbs 34 (i.e., a first subset of barbs 34) may be angled towards the distal end 16 and the free end 35 of one or more other barbs 34 (i.e., a second subset of barbs 34) may be angled towards the proximal end 14, as desired. In some instances, the barbs 34 may be angled such that the free end 35 is directed towards or pointed in the direction of likely migration. In the case of an esophageal stent, the free end 35 of the barbs 34 may be pointed toward the distal end 16 of the stent 10 to be directed towards the stomach upon implantation in the esophagus.

The barbs 34 may be attached to the filaments 36 at a base or attachment end 37 by welding, gluing, wrapping, or by other suitable methods. In other embodiments, the barbs 34 may be formed as a unitary portion of filaments 36 with the free end 35 extending from the filament 36. In some embodiments, the barbs 34 may be attached to the filaments 36 at or adjacent to the cross points 44 where a filament portion extending in a first helical direction crosses a filament portion extending in a second helical direction, opposite the first helical direction. In other embodiments, the barbs 34 may be attached to the filaments 36 at a point intermediate to two cross-points 44. It is further contemplated that the stent 10 may include a plurality of barbs 34 attached at a variety of different locations relative to the cross-points 44. In other words, all of the barbs 34 need not all be attached at similar locations (e.g., all on cross-points 44 or all intermediate to two adjacent cross-points 44).

In some cases, the barbs 34 may be positioned on the stent 10 in a predetermined pattern or arrangement. The barbs 34 may be positioned along a length of the stent 10 and/or about the circumference of stent 10, as desired. It is contemplated that the barbs 34 may be positioned in any number of symmetric or asymmetric configurations along the length and/or circumference of the stent 10. FIG. 1 shows one illustrative example in which the barbs 34 are relatively evenly spaced along a length and circumference of the stent 10. In some cases, the barbs 34 may be positioned over only a portion of the length (and/or circumference) of the stent 10. For example, in some cases, the barbs 34 may be positioned on only the intermediate region 18, one or both of the end regions 20, 22, or various combinations thereof. It is further contemplated that the barbs 34 may vary in length, as will be described in more detail below.

The barbs 34 may be formed from a superelastic or pseudo-elastic material (such as, but not limited to, Nitinol) of sufficient strength to allow the barbs 34 to interact with body lumen tissue without becoming deformed. In some cases, the barbs 34 may be formed of a shape memory material (such as, but not limited to, Nitinol) to provide the barbs 34 with shape memory properties. Other suitable materials may include polymers, metals, ceramics, composites, and/or combinations thereof. In some cases, the barbs 34 may be formed from a material combination which behaves like a temperature sensitive bimetallic strip. In some cases, the barbs 34 may include a first metal and a second metal, wherein the first metal has a different coefficient of thermal expansion than that of the second metal. This may cause outward protrusion (e.g., radial extension) of the barbs 34 from the stent 10 when the barbs 34 are in contact with body temperature tissue but allow the barbs 34 to remain straight or in a radially contracted state at room temperature. This may allow loading and deployment interaction with a sheath or other delivery device.

The barbs 34 may be formed such that they are biased or predisposed to a deployment configuration in which the barbs 34 angle radially outward away from the outer surface of the elongated tubular member 12. In other words, the "remembered" shape or orientation of the barbs 34 may be radially extending outward from the body 12 of the stent 10. However, this orientation of the barbs 34 may cause the barbs 34 to adversely interact with a sheathed delivery system causing the potential for device malfunction. Thus, it is contemplated that the braided, knitted or woven structure of the stent 10 may be used to retain the barbs 34 in a delivery configuration to minimize or prevent the barbs 34 from adversely interacting with the sheathed delivery system. For example, the barbs 34 may be connected to the filaments 36 at intermittent points around the length and/or circumference of the stent 10. The barbs 34 may be oriented such that their deployment configuration has them protruding radially outward from the stent body 12, as shown in FIG. 1. Prior to loading the stent 10 in a sheath of a delivery system, the barbs 34 may be tucked under an adjacent filament 36 (e.g., biased or temporarily deformed) as described in more detail with respect to FIGS. 2-4. In some cases, the adjacent filament 36 may be located on the opposite side of the stent cell to which the barb 34 is attached and extend generally parallel to the filament 36 which the barb 34 is attached to, or the adjacent filament 36 may be the filament crossing across (e.g., over or under) the filament 36 which the barb 34 is attached to.

Figure 2:
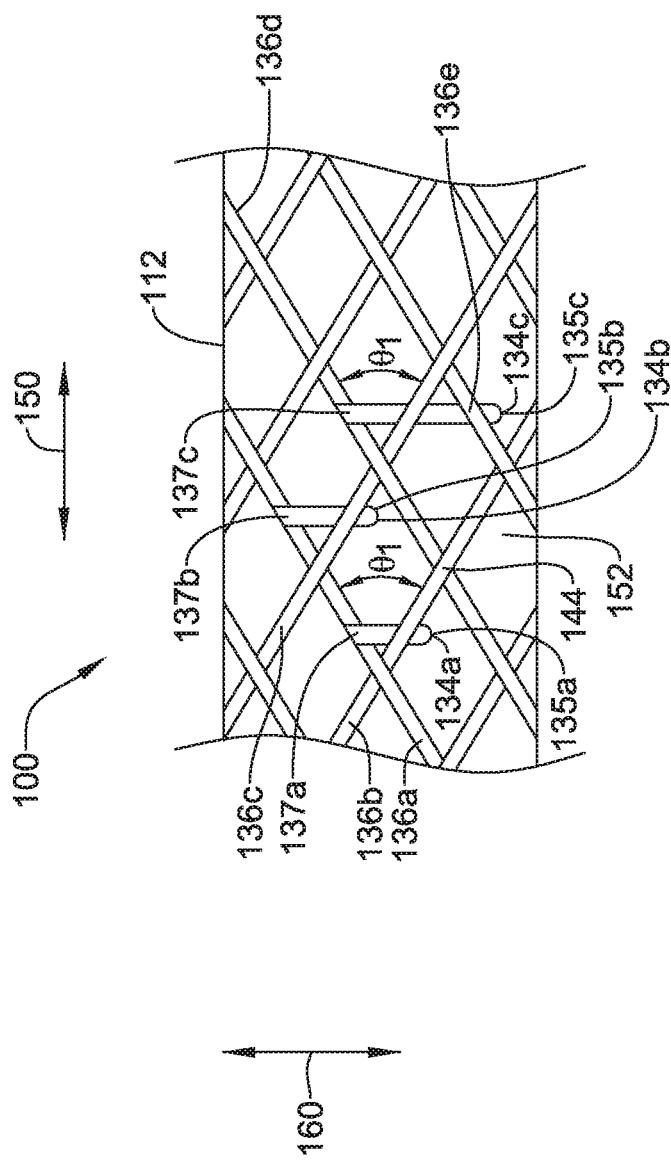
FIG. 2 is a partial side view of an illustrative stent anchoring system in a collapsed configuration.

FIG. 2 illustrates a side view of a portion of an illustrative stent 100, similar to the stent 10, in a collapsed configuration. The stent 100 may include a stent body 112 and be similar in form and function to the stent 10 described herein. The stent 100 may have a woven or braided structure, fabricated from a number of filaments or struts 136. The filaments 136 may form a plurality of generally diamond shaped cells 152 therebetween. However, other cell 152 shapes are contemplated. The cells 152 are openings or interstices extending through the stent body 112 having a perimeter defined by the struts of filaments 136. In the collapsed configuration, the major axis of the cell 152 may extend in the longitudinal direction, as shown at arrow 150. To collapse the stent 100 for delivery the stent 100 may be stretched (longitudinally 150) and compressed (radially 160) causing elongation of the cells 152 in the longitudinal direction 150 and contraction of the cells 152 in the circumferential direction. As the stent 100 is moved between the collapsed configuration (FIG. 2) and an expanded configuration (FIGS. 3 and 4), such as during deployment of the stent 100, the shape of the cell 152 may change such that the cell 152 is elongated in the circumferential direction, as shown at arrow 160 and contracted in the longitudinal direction 150.

The stent 100 may include a plurality of retention features or barbs 134a, 134b, 134c (collectively, 134) (e.g., tines, quills, or barbs) attached to one or more of the filaments 136. The barbs 134 may be similar in form and function to the barbs 34 described herein. The barbs 134a, 134b, 134c may be attached to a filament 136 at a first end 137a, 137b, 137c (collectively, 137) and extend towards a second, free end 135a, 135b, 135c (collectively, 135). In some instances, the barbs 134 may vary in length. For example, the illustrative stent 100 includes two barbs 134a, 134b, each having a similar first length, affixed to a first filament 136a and a third barb 134c having a second length affixed to another filament 136d. The second length may be greater than the first length. This is just an example. The stent 100 may include any number of barbs 134 having any combination of lengths thereof. In the illustrative embodiment of FIG. 2, the free ends 135 of the barbs 134 all point in the same direction. This is not required. The free ends 135 of the barbs 134 may point in direction desired. Further, all of the barbs 134 need not be affixed to filaments 136 wound in the same helical direction.

Figure 3:
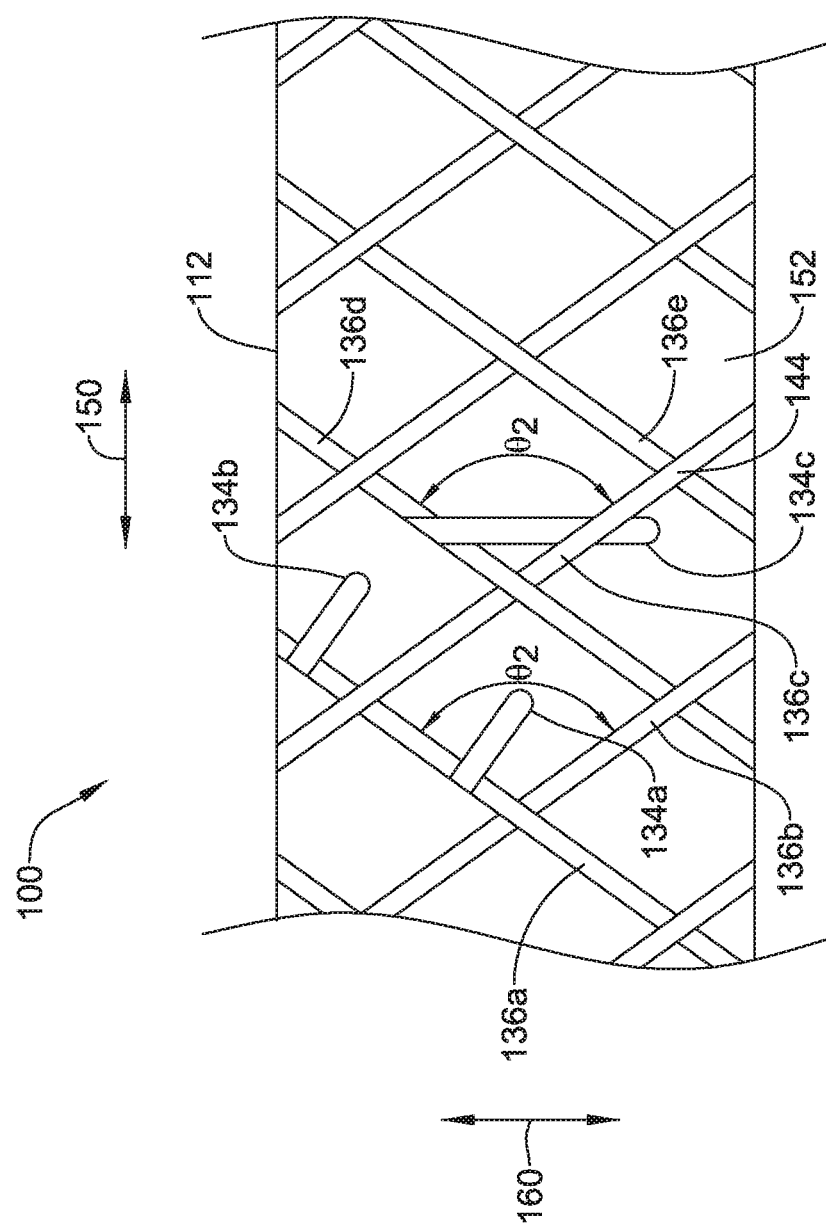
FIG. 3 is a partial side view of the illustrative stent anchoring system of FIG. 2 in a partially deployed configuration.
Figure 4:
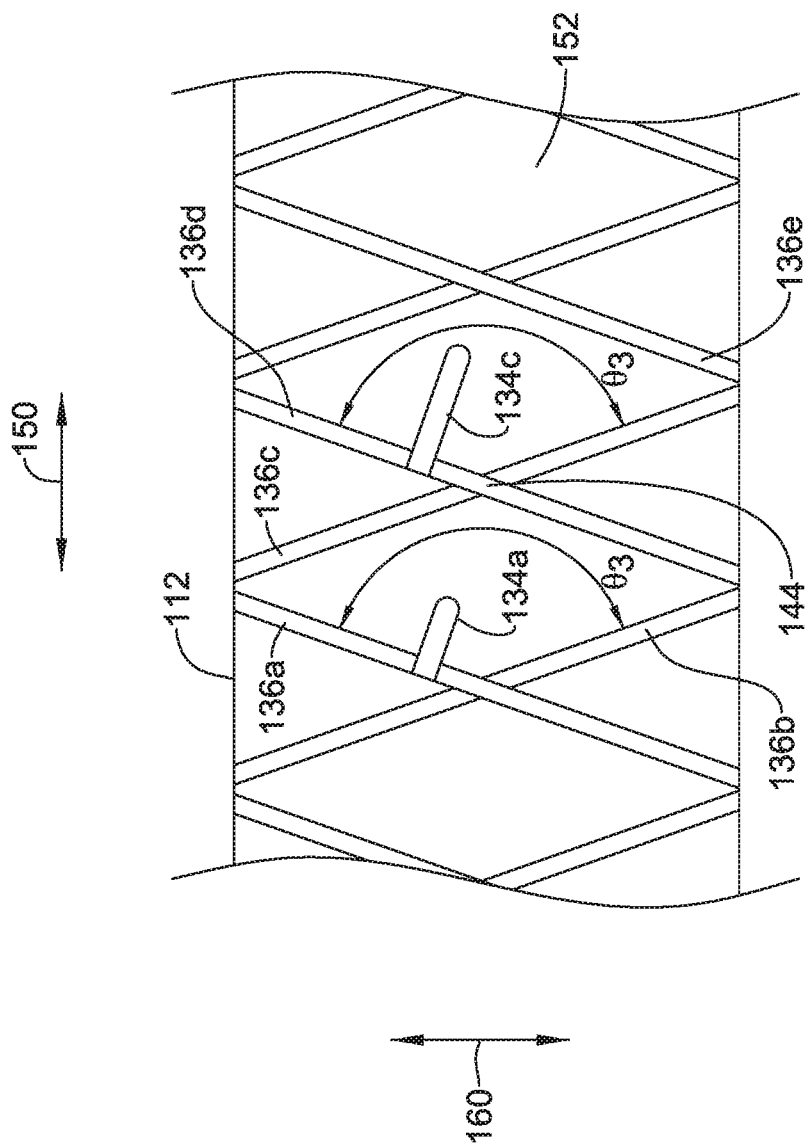
FIG. 4 is a partial side view of the illustrative stent anchoring system of FIGS. 2 and 3 in a fully deployed configuration.

The barbs 134 may be affixed to the filaments 136 at locations intermediate to the filament cross-points 144, although this is not required. As described herein, when the barbs 134 are attached to the stent 100, they may be biased or predisposed to extend radially outward from the stent body 112 when unconstrained. To protect the delivery system from damage from the barbs 134, the free ends 135 of the barbs 134 may be tucked or secured under an adjacent filament 136, as shown in FIG. 2, such that they do not protrude radially outward beyond the outer surface of the tubular body of the stent 10. The barbs 134 may be initially tucked when the stent 100 is in its deployed state and the cells 152 are at their minimum radial dimension 160 and/or maximum longitudinal dimension 150. The stent 100 may be gradually sheathed (and hence elongated and radially compressed) as the barbs 134 are simultaneously tucked, such that the barbs 134 systematically become trapped radially inside (e.g., under) the filaments 136 of the stent 100 as the cell 152 changes shape (e.g., reduces in the radial dimension 160 and elongates in the longitudinal direction 150). While the general shape of the cell 152 remains the same in the collapsed and the expanded configurations (e.g., the cell 152 remains a diamond), the dimensions, area and/or angles of the cell 152 may change resulting in what is referred to herein as a shape or profile change. For example, the angle (e.g., braid angle) at the cross-over points between intersecting filaments may increase as the stent 100 expands from the collapsed configuration (FIG. 2) to the expanded configuration (FIGS. 3 and 4). As used herein, "braid angle" is intended to mean the angle between two interwoven filaments 136 or filament portions extending in opposite helical directions at a cross-over point along the longitudinal axis of the stent 100.

The stent 100, including the tucked barbs 134 (as shown in FIG. 2), may allow for a stent 100 with anchoring features to be delivered at an anatomical location in such a manner that the barbs 134 do not interact with the sheath of the delivery system or protrude outward beyond the outer surface of the tubular body 112 of the stent 100 formed by the interwoven filament(s). The barbs 134 may only become active (e.g., extend radially from the body 112 of the stent 100) when the stent 100 is unsheathed. The act of unsheathing changes the cell shapes 152 of the stent 100 (e.g., changes the area of the cells 152 and/or the angles between intersecting filaments or filament portions) and allows the trapped barbs 134 to be released and interact with the body lumen wall at the deployed location. As shown in FIG. 2, the filaments 136 may be arranged at a first braid angle $\theta_1$ in a delivery or collapsed configuration.

A first barb 134a may be affixed to a filament 136a wound in a first helical direction. In a delivery or collapsed configuration, the first barb 134a may be tucked underneath an adjacent filament 136b (e.g., an adjacent filament crossing across or intersecting the filament 136a). In other words, the first barb 134a may be disposed radially inwards of the adjacent filament 136b. In some cases, the adjacent filament 136b may be wound in a second helical direction, generally opposite to the first helical direction of the filament 136a to which the first barb 134a is attached and intersect the first filament 136a.

A second barb 134b may be affixed to a filament 136a wound in a first helical direction. While the second barb 134b is illustrated as affixed to the same filament 136a as the first barb 134a, the second barb 134b may be affixed to any filament 136 desired. In a delivery or collapsed configuration, the second barb 134b may be tucked underneath an adjacent filament 136c (e.g., an adjacent filament crossing across or intersecting the filament 136a). In other words, the first barb 134a may be disposed radially inwards of the adjacent filament 136c. As the second barb 134b is circumferentially and/or longitudinally offset from the first barb 134a, the second barb 134b may be secured under a different filament 136c from the first barb 134a (which is secured under filament 136b). In some cases, the adjacent filament 136b may be wound in a second helical direction, generally opposite to the first helical direction of the filament 136a to which the second barb 134b is attached and intersect the first filament 136a.

A third barb 134c may be affixed to a filament 136d wound in a first helical direction, which may be parallel to the filament 136a. In a delivery or collapsed configuration, the third barb 134c may be tucked underneath an adjacent filament 136c and another filament 136e due to its length. In other words, the third barb 134c may be disposed radially inwards of the adjacent filaments 136c, 136e. In some cases, the adjacent filament 136c may be wound in a second helical direction, generally opposite to the first helical direction of the filament 136d to which the third barb 134c is attached. The other filament 136e under which the third barb 134c is tucked may be wound in the same helical direction as the filament 136d and extend generally parallel to the filament 136d to which the third barb 134c is attached.

It is contemplated that barbs 134 having varying lengths may be provided on the same stent 100 such that the amount of anchoring support can vary with the anatomical region being stented. For example, if the stent 100 is deployed into a region of small relative diameter (compared the fully expanded stent 100) the braid cell profile 152 alters only slightly and potentially only shorter barbs may be released. The stent 100 in this orientation would have a relatively high radial force (as it is not fully deployed). This, coupled with the shorter barbs 134a, 134b, may be sufficient to avoid and/or minimize migration of the stent 100. Alternatively, if the stent 100 is deployed into a region of large relative diameter (e.g., similar to the diameter of the fully expanded stent 100) the braid cell profile 152 may alter significantly and potentially short to medium to large barbs 134 may be progressively released. The stent 100 in this orientation would have a relatively low radial force (as it is fully deployed). This, coupled with a longer barb 136c array may be sufficient to avoid and/or minimize migration of the stent 100. In some instances, the length of the barbs 134 may be in the range of 1.5 millimeters to 5.5 millimeters (mm). A relatively short length barb 134 may have a length in the range of 1.5 to 2.5 mm, a medium length barb 134 may have a length in the range of 2.5 to 3.5 mm, and a long length barb 134 may have a length in the range of 3.5 to 5.5 mm, for example. These are just examples. The length of the barb 134 may be determined by the contracted and expanded dimensions of the cell 152 and/or the size of the stent 100 and can be shorter than 1.5 mm or greater than 5.5 mm, as desired.

In some cases, the stent 100 may be centered adjacent to a tumor or another anatomical region that has diametrical variations over a length of the stent 100. Various anatomical structures (such as, but not limited to, a tumor) may result in the stent 100 assuming (at least initially) a dog boned shape (or a shape similar to the stent 10 illustrated in FIG. 1), a tapered shape, or other shape having varying diameters (and/or varying degrees of stent deployment). In the case of a dog-boned shape, it may be desirable to deploy shorter barbs 134 in an intermediate region where there is a greater radial force applied (because the stent 100 is not fully deployed) to the vessel by the stent 100 and longer barbs 134 adjacent the end regions where the radial force applied to the vessel by the stent 100 may be less than the intermediate region. It is contemplated that longer barbs 134 may extend farther into the tissue and provide more anchoring (or anti-migration support) than shorter barbs 134. It is further contemplated that including barbs 134 of varying length may also be used in stents 100 where the shape of the stent 100 may vary over time. For example, in long term implants, the diameter of the stent 100 may change (e.g., increase) over time. Additional anchoring may be required as the diameter increases and less radial force is applied to the vessel wall by the stent 100. In such an instance, the inclusion of longer or varying length barbs 134 that can be deployed over time as the diameter of the stent 100 increases may provide additional anchoring over time. It is further contemplated that the location at which the barbs 134 are attached to the stent 100 (e.g., distance between cross-points) may also influence when the barbs 134 are deployed. As can be appreciated, for a barb 134 having a constant length, the farther the barb 134 is attached from the adjacent filament, the quicker it will be deployed as the stent 100 is expanded.

FIG. 3 illustrates a side view of the illustrative stent 100 of FIG. 2 in a partially deployed or expanded configuration in which the diameter of the stent has increased from the collapsed, delivery configuration. As the stent 100 radially expands and/or longitudinally contracts, the profile of the cells 152 may change (e.g., the area and/or angles of the cells 152 may change). For example, the filaments 136 may be arranged at a second braid angle $\theta_2$ in the partially deployed or expanded configuration. The second braid angle $\theta_2$ may be greater than the first braid angle $\theta_1$. Furthermore, the area of the cells 152 may increase from an area of the cells 152 in the delivery or collapsed configuration to the partially deployed or expanded configuration. As can be seen in FIG. 3, the shorter barbs 134a, 134b have been released from under adjacent filaments 136b, 136c and deployed and the free ends 135a, 135b are now extending radially outward from the outer surface of the body 112 of the stent 100 while the free end 135c of the longer barb 134c is still secured under an adjacent filament 136c.

Further deployment of the stent 100 (e.g., further radial expansion and/or longitudinal contraction of the stent 100), as shown in FIG. 4, further changes the profile of the cells 152 (e.g., further increases area and/or angles of the cells 152) which may release the longer barb 134c from under adjacent filament 136c such that the barb 134c also extends radially outward from the outer surface of the body 112 of the stent 100. For example, the filaments 136 may be arranged at a third braid angle $\theta_3$ in the fully deployed or expanded configuration. The third braid angle $\theta_3$ may be greater than the first braid angle $\theta_1$ and the second braid angle $\theta_2$. Furthermore, the area of the cells 152 may increase from the area of the cells 152 in the delivery or collapsed configuration as well as the partially deployed or expanded configuration. Thus, the area of the cells 152 in the fully deployed or expanded configuration may be greater than the area of the cells 152 in the delivery or collapsed configuration and/or the partially deployed or expanded configuration.

Figure 5:
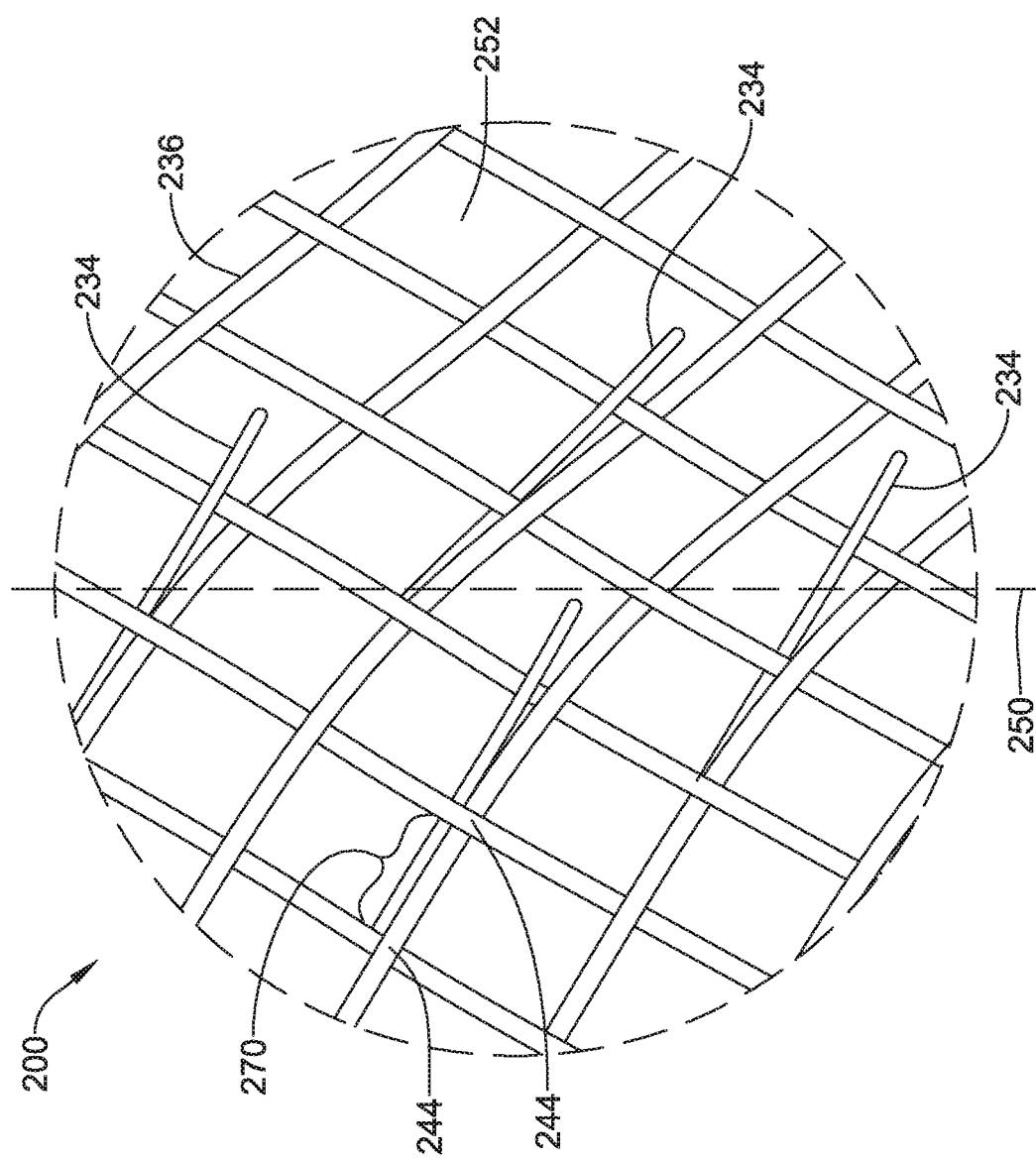
FIG. 5 is a perspective view of another illustrative stent anchoring system.

FIG. 5 illustrates a perspective view of another illustrative stent 200 in an expanded (e.g., deployed) configuration. The stent 200 may include a tubular stent body extending along a longitudinal axis 250 and be similar in form and function the stent 10 described herein. The stent 200 may have a woven or braided structure, fabricated from a number of interwoven filaments or struts 236. The filaments 136 may form a plurality of generally diamond shaped cells 252. However, other cell 252 shapes are contemplated. The stent 200 may include a plurality of retention features 234 (e.g., tines, quills, or barbs) attached to one or more of the filaments 236. The barbs 234 may be similar in form and function to the barbs 34, 134 described herein.

As can be seen in FIG. 5, the barbs 234 may extend radially outward from an outer surface of the stent 200. While FIGS. 2-4 illustrate the barbs 134 as being attached at a terminal end of the barb 134 to the stent 100, FIG. 5 illustrates the barbs 234 can be affixed to the stent 200 along a portion of the length of the barb 234. Securing the barbs 234 along a length (as opposed to securing at an end point) may provide a more rigorous means of attachment. In some cases, the barbs 234 may be secured along a length 270 approximately equivalent to a length between two adjacent cross-points 244. This is just an example.

Figure 6:
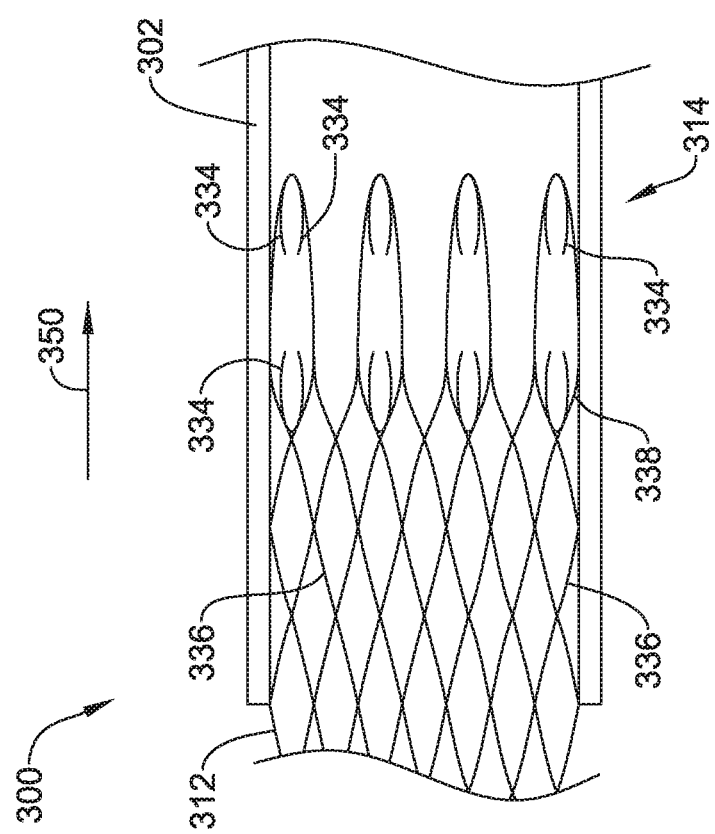
FIG. 6 is a side view of a portion of another illustrative stent anchoring system in a first configuration.

FIG. 6 illustrates a side view of another illustrative stent 300 in a collapsed configuration within a delivery sheath 302. The stent 300 may include a tubular stent body 312 and be similar in form and function to the stent 10 described herein. The stent 300 may have a woven or braided structure, fabricated from a number of filaments or struts 336. The stent 300 may include a plurality of retention features 334 (e.g., tines, quills, or barbs) attached to one or more of the filaments 336. The barbs 334 may be similar in form and function to the barbs 34, 134, 234 described herein. In some instances, the barbs 334 may include more than one barb 334 attached at the same location, as shown in FIG. 6.

Figure 7:
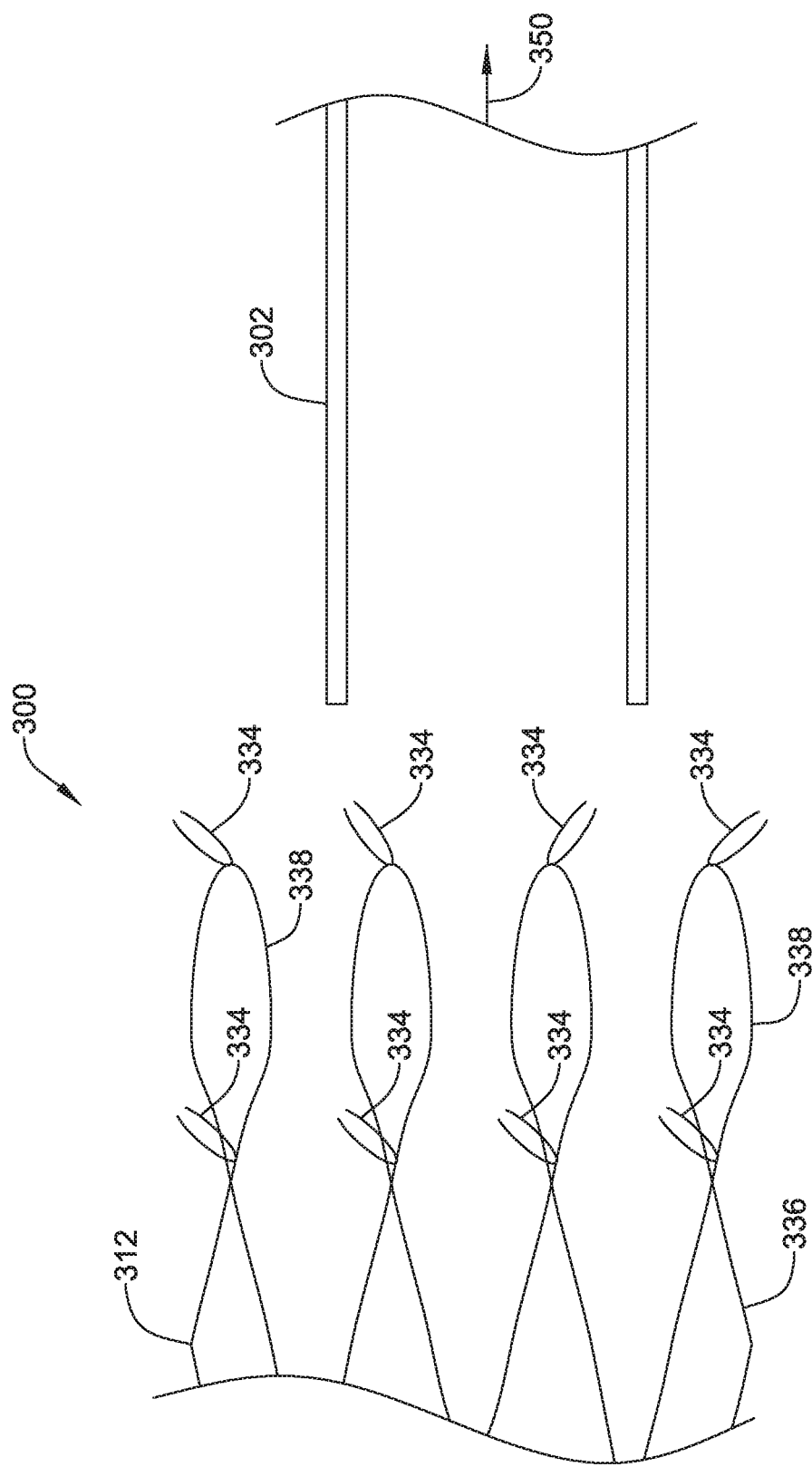
FIG. 7 is a side view of a portion of the illustrative stent anchoring system of FIG. 6 in a second configuration.

In some embodiments, the barbs 334 may be concentrated adjacent to a proximal end 314 of the stent 300. Alternatively, or additionally, the barbs 334 may be concentrated adjacent to a distal end (not explicitly shown) of the stent 300. The barbs 334 may be retained in a collapsed configuration by the delivery sheath 302. Once the target vessel has been reached, the sheath 302 may be proximally retracted, as shown at arrow 350. Once the sheath 302 has been removed from the region including the barbs 334, as shown in FIG. 7, the barbs 334 may be deployed such that they extend radially from the body 312 of the stent 300 to engage the tissue. In some instances, a portion of the stent 300, such as the distal end portion (not shown) opposite the end including the barbs 334 may be deployed and expanded in the body lumen prior to removing the sheath 302 to deploy the barbs 334 at the proximal end 314 of the stent 300. While FIGS. 6 and 7 illustrate two circumferential groups or banks of barbs 334, it is contemplated that the stent 300 may include only a single bank of barbs 334 or more than two banks of barbs 334, as desired. Further the groups of barbs 334 need not be arranged circumferentially about the stent 300. As described above, the barbs 334 may be oriented in any longitudinal and/or circumferential arrangement desired.

Figure 8:
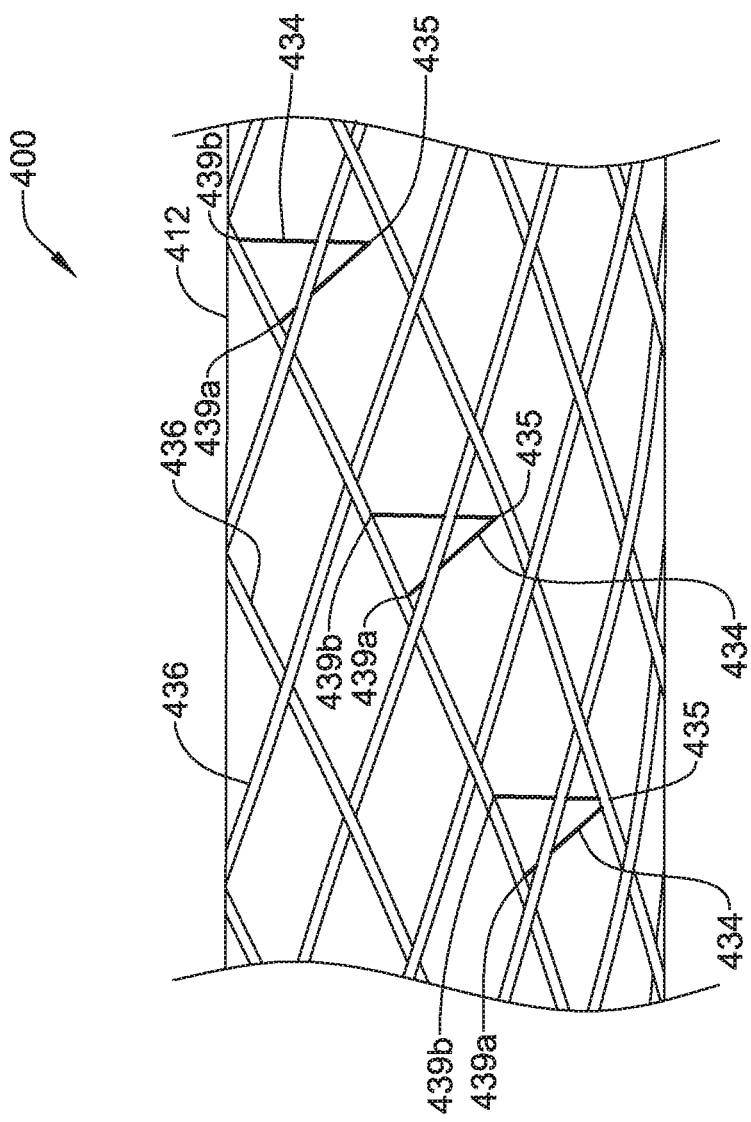
FIG. 8 is a side view of a portion of another illustrative stent anchoring system in a first configuration.
Figure 9:
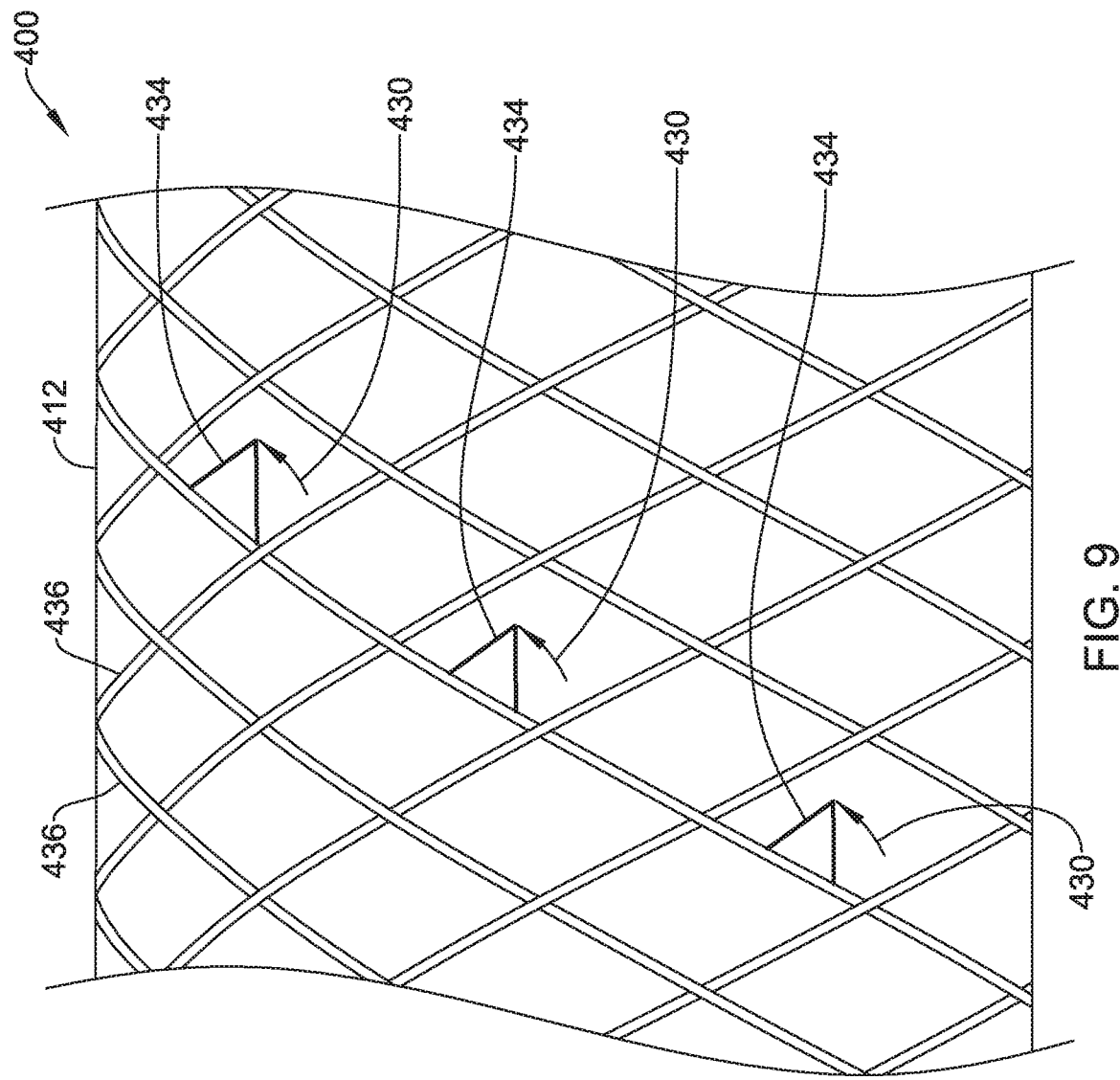
FIG. 9 is a side view of a portion of the illustrative stent anchoring system of FIG. 8 in a second configuration.

FIG. 8 illustrates a side view of another illustrative stent 400 in a collapsed configuration. FIG. 9 illustrates a side view of the illustrative stent 400 of FIG. 8 in a radially expanded configuration. The stent 400 may include a tubular stent body 412 and be similar in form and function to the stent 10 described herein. The body 412 of the stent 400 may have a woven or braided structure, fabricated from a number of interwoven filaments or struts 436 defining cells 452 therebetween. The stent 400 may include a plurality of retention features 434 (e.g., tines, quills, or barbs) attached to one or more of the filaments 436. The barbs 434 may be similar in form and function to the barbs 34, 134, 234, 334 described herein. In some cases, the barbs 434 may be formed from a filament or wire. Both ends 439a, 439b of the filament or wire of the barb 434 may be affixed to the filament 436. The barbs 434 may form a generally pointed or triangular shape with the filaments 436. However, other shapes are also contemplated. A region intermediate to the ends 439a, 439b may from the free end or portion 435 which may be configured to engage bodily tissue.

The barbs 434 may be attached to the stent 400 such that they may be biased or predisposed to extend radially outward from the outer surface of the stent body 412. To protect the delivery system from damage from the barbs 434, the free end 435 of the barbs 434 may be tucked or secured under an adjacent filament 436 (i.e., radially inward of the adjacent filament 436), as shown in FIG. 8, such that the barbs 434 do not protrude radially out beyond the outer surface of the body 412. As the stent 400 is radially expanded, the barbs 434 may become unconstrained from the adjacent filament 436 and rotate 430 such that the free end 435 extends radially outward beyond the body portion 412 of the stent 400, as shown in FIG. 9. The spaced apart ends 439a, 439b may allow the barbs 434 to function as a hinge or spring mechanism. For example, the protrusion angle of barbs 434 may be varied (e.g., increased or decreased) if acute repositioning or removal of the stent 400 is required. In some cases, with the correct placement on the filament 436, the barbs 434 may be retrapped under the filaments (as shown in FIG. 8) to facilitate removal and or repositioning of the stent 400.

Figure 10:
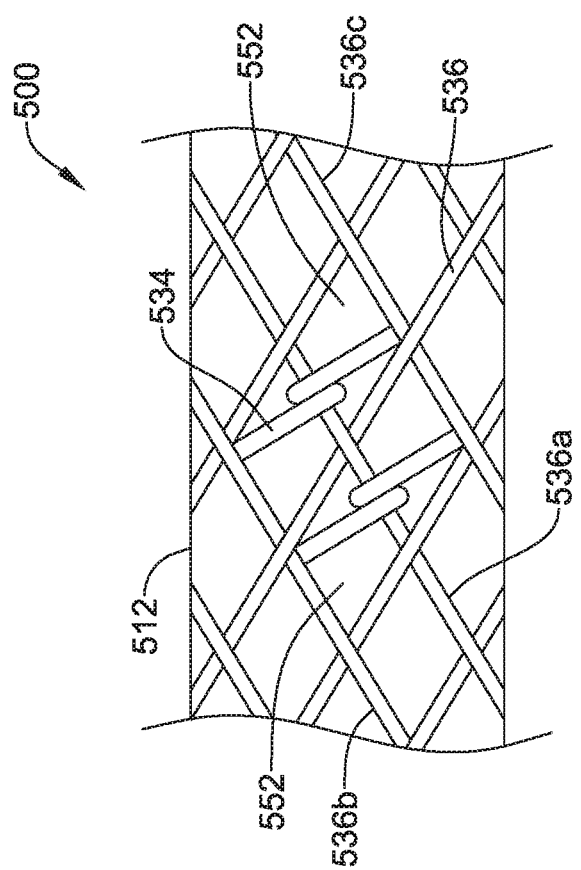
FIG. 10 is a perspective view of a portion of an illustrative stent including an anchoring system in a first configuration.

FIG. 10 illustrates a side view of another illustrative stent 500 in a collapsed configuration. FIG. 11 illustrates a side view of the illustrative stent 500 of FIG. 10 in a radially expanded configuration. The stent 500 may include a tubular stent body 512 and be similar in form and function to the stent 10 described herein. The body 512 of the stent 500 may have a woven or braided structure, fabricated from a number of interwoven filaments or struts 536 defining cells 552 therebetween. The stent 500 may include a plurality of retention features 534 (e.g., tines, quills, or barbs) attached to one or more of the filaments 536. The barbs 534 may be similar in form and function to the barbs 34, 134, 234, 334, 434 described herein. In some cases, the barbs 534 may be formed from a filament or wire having a coiled portion 540 (see FIG. 10A) wrapped or wound around one of the filaments 536, such as a first filament 536a. The coiled portion 540 may be welded or otherwise affixed to the filament 536a in some instances. The filament forming the barb 534 may include a first end portion 538a extending from the coiled or base portion 540 to a first tip or free end 535a and/or a second end portion 538b extending from the coiled or base portion 540 to a second tip or free end 535b.

The barbs 534 may be attached to the stent 500 such that they may be biased or predisposed to extend radially outward from the outer surface of the stent body 512. To protect the delivery system from damage from the barbs 534, the free end(s) 535a/535b of the barbs 534 may be tucked or secured under an adjacent filament 436 (i.e., radially inward of the adjacent filament 536), as shown in FIG. 10, such that the barbs 534 do not protrude radially out beyond the outer surface of the body 512. For example, as shown in the cross-section of FIG. 10A, the first free end 535a may be arranged radially inward of a second filament 536b and the second free end 535b may be arranged radially inward of a third filament 536c, such that the filaments 535b/535c restrain the free ends 535a/535b from extending radially outward of the outer surface of the stent body 512.

Figure 11:
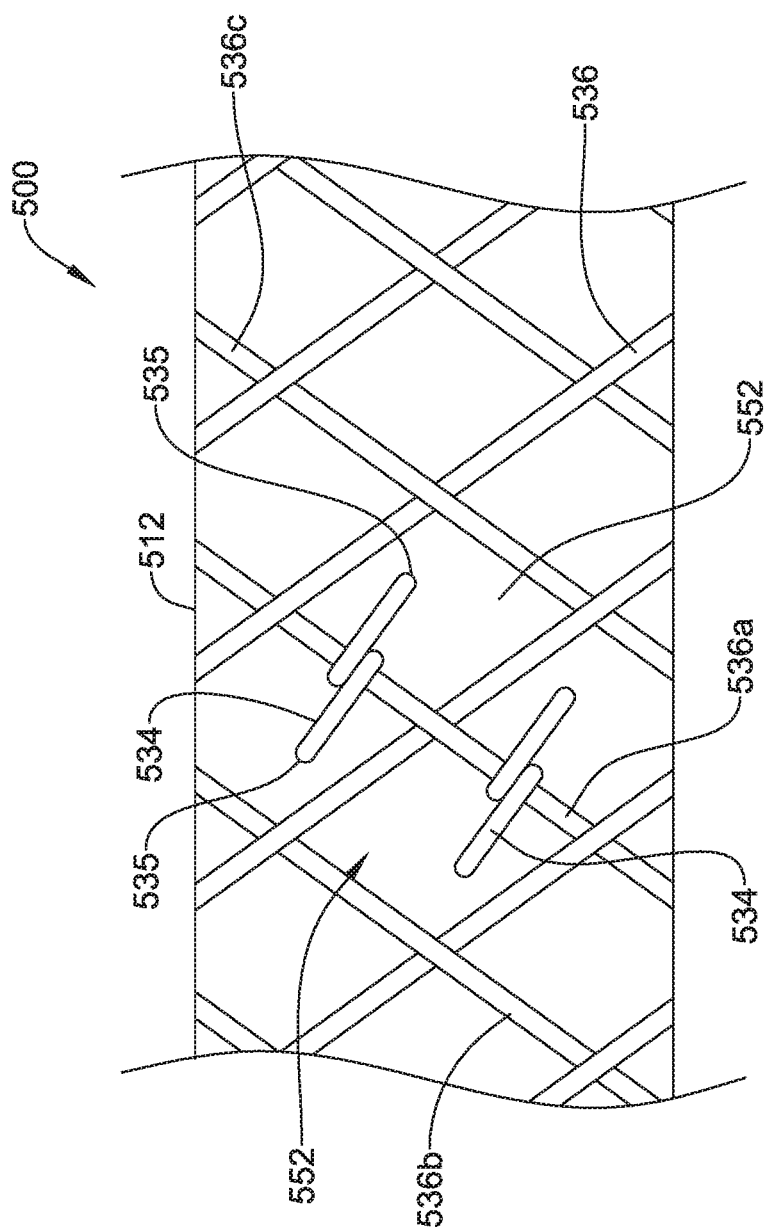
FIG. 11 is a perspective view of a portion of the illustrative stent of FIG. 10 including the anchoring system in a second configuration.
Figure 11A:
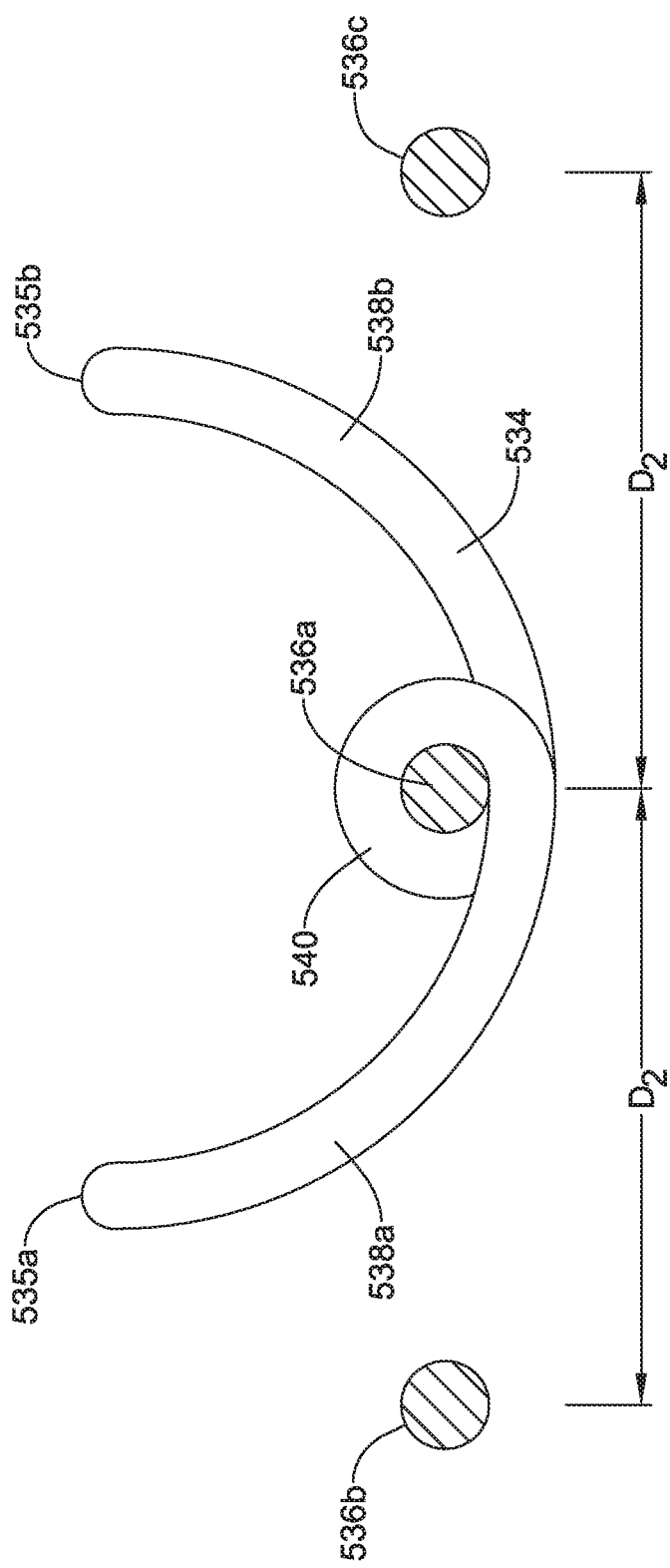
FIG. 11A is a cross-sectional view of a portion of the stent of FIG. 11 including the anchoring system in the second configuration.

As the stent 500 is radially expanded, the free ends 535a/535b of the barbs 534 may become unconstrained from the adjacent filaments 536b/536c and spring radially outward such that the free ends 535a/535b extend radially outward beyond the body portion 512 of the stent 500, as shown in FIGS. 11 and 11A.

Figure 10A:
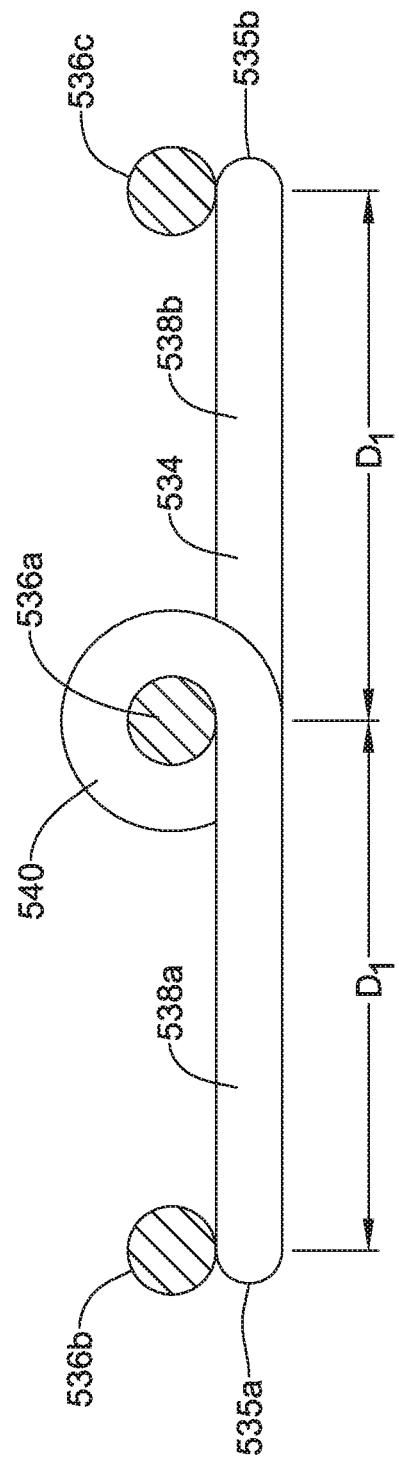
FIG. 10A is a cross-sectional view of a portion of the stent of FIG. 10 including the anchoring system in the first configuration.

As the stent 500 radially expands from the delivery or radially collapsed configuration in FIGS. 10 and 10A to the radially expanded configuration in FIGS. 11 and 11A, the profile of the cells 552 may change (e.g., the area and/or angles of the cells 552 may change). For example, as discussed above, the filaments 536 may be arranged at a first braid angle in the radially collapsed configuration and a second braid angle, greater than the first braid angle, in the radially expanded configuration. Additionally, the area of the cells 552 may increase from an area of the cells 552 in the radially collapsed configuration to the radially expanded configuration. Furthermore, as shown in FIGS. 10A and 10B, the distance between the attachment point (e.g., the coil or base portion 540 on the first filament 536a to the adjacent filaments 536b/536c may change as the stent 500 is radially expanded. For example, the distance between the attachment point (e.g., the coil or base portion 540 on the first filament 536a to the point of the adjacent filaments 536b/536c under which the free ends 535a/535b are positioned may be a first distance $D_1$ in the radially collapsed configuration (FIG. 10A) and the distance between the attachment point (e.g., the coil or base portion 540) on the first filament 536a to the point of the adjacent filaments 536b/536c under which the free ends 535a/535b were positioned may be a second distance $D_2$ in the radially expanded configuration (FIG. 11A). The second distance $D_2$, which may be greater than the first distance $D_1$, may be large enough to allow the free ends 535a/535b to clear the filaments 536b/536c and deflect radially outward of the outer surface of the body 512 of the stent 500. In other words, the first distance $D_1$ may be less than the length of the barb 534 from the base or coiled portion 540 to the free end 535 whereas the second distance $D_2$ may be greater than the length of the barb 534 from the base or coiled portion 540 to the free end 535.

The stents, delivery systems, and the various components thereof, may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; and the like; or any other suitable material.

Some examples of suitable polymers for the stents or delivery systems may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like.

In at least some embodiments, portions or all of the stents or delivery systems may also be doped with, made of, or otherwise include a radiopaque material. Radiopaque materials are generally understood to be materials which are opaque to RF energy in the wavelength range spanning x-ray to gamma-ray (at thicknesses of <0.005"). These materials are capable of producing a relatively dark image on a fluoroscopy screen relative to the light image that non-radiopaque materials such as tissue produce. This relatively bright image aids the user of the stents or delivery systems in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the stents or delivery systems to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent, the stent comprising:
   an elongated tubular member comprising at least one filament interwoven to form a plurality of cells, the elongated tubular member configured to move between a collapsed configuration and an expanded configuration; and
   at least one barb fixed to the at least one filament, the at least one barb having a first end, a second end, and a length extending therebetween, the at least one barb fixed to the at least one filament at least along a portion of the length of the at least one barb, wherein at least the first end is free of attachment to the elongated tubular member in the expanded configuration;
   wherein the free first end of the at least one barb is configured to be positioned radially inward of and under an adjacent winding of the at least one filament when the elongated tubular member is in the collapsed configuration and to extend radially away from the elongated tubular member when the elongated tubular member is in the expanded configuration.

2. The stent of claim 1, wherein in the collapsed configuration the plurality of cells have a first profile and in the expanded configuration the plurality of cells have a second profile different from the first profile, wherein the first profile of the plurality of cells has a major dimension extending along a longitudinal axis of the elongated tubular member.

3. The stent of claim 2, wherein the second profile of the plurality of cells has a major dimension extending along a circumference of the elongated tubular member.

4. The stent of claim 1, wherein the at least one barb comprises a wire.

5. The stent of claim 1, wherein the second end of the at least one barb is attached to the at least one filament.

6. The stent of claim 5, wherein the portion of the length of the at least one barb fixed to the at least one filament is equivalent to a length between two adjacent cross-points defining one of the plurality of cells.

7. The stent of claim 6, wherein the elongated tubular member has an inner surface and an outer surface, the inner surface defined by an inner surface of the at least one filament, wherein the second end and portion of the length of the at least one barb are fixed to the inner surface of the at least one filament.

8. The stent of claim 1, wherein each barb has a width transverse to the length, wherein the adjacent winding extends over an entirety of the width of the barb when the elongated tubular member is in the collapsed configuration.

9. The stent of claim 1, wherein the at least one barb comprises a wire helically wound around the at least one filament.

10. The stent of claim 9, wherein a middle portion of the wire forming each barb is helically wound around the at least one filament, and both first and second ends of the at least one barb are free and biased to extend radially outward from the elongated tubular member when unconstrained.

11. The stent of claim 10, wherein when the elongated tubular member is in the collapsed configuration, the free first end is disposed radially inward of a second filament and the second free end is disposed radially inward of a third filament.

12. The stent of claim 1, wherein the at least one barb comprises a material combination which behaves like a temperature sensitive bimetallic strip.

13. The stent of claim 1, wherein the at least one barb comprises a plurality of barbs spaced along a length and a circumference of the elongated tubular member.

14. The stent of claim 1, wherein the at least one barb comprises a plurality of barbs, wherein at least some of the plurality of barbs have a first length and at least some of the plurality of barbs have a second length different from the first length.

15. A stent, the stent comprising:
- an elongated tubular member comprising at least one filament interwoven to form a plurality of cells, the elongated tubular member configured to move between a collapsed configuration and an expanded configuration; and
- a plurality of barbs fixed to the at least one filament and comprising a shape memory wire, the plurality of barbs each having a first end, a second end, and a length extending therebetween, each barb fixed to the at least one filament at least along a portion of the length of the barb, at least the first end of each barb is free and biased to extend radially outward from the elongated tubular member when unconstrained;
- wherein in the collapsed configuration the at least one filament applies a radially inward constraining force to the free first end of each barb such that the free first end is constrained radially inward of the at least one filament and as the elongated tubular member moves from the collapsed configuration to the expanded configuration the free first end of at least some of the plurality of barbs is unconstrained by the at least one filament and extends radially outward from the elongated tubular member.

16. The stent of claim 15, wherein each cell is defined by junctions of the at least one filament, and wherein at least some of the plurality of barbs are fixed to the at least one filament between and spaced away from adjacent junctions.

17. The stent of claim 15, wherein the second end of at least some of the plurality of barbs is attached to the at least one filament.

18. The stent of claim 15, wherein at least some of the plurality of barbs comprises a wire helically wound around the at least one filament, wherein a middle portion of the wire is helically wound around the at least one filament, and both first and second ends are free and biased to extend radially outward from the elongated tubular member when unconstrained.

19. A stent, the stent comprising:
- an elongated tubular member comprising at least one filament interwoven to form a plurality of cells defined by junctions of the at least one filament, the elongated tubular member configured to move between a collapsed configuration and an expanded configuration; and
- at least one barb fixed to the at least one filament, the at least one barb having a first end, a second end, and a length extending therebetween, the at least one barb fixed to the at least one filament at least along a portion of the length of the at least one barb, wherein at least the first end of the at least one barb is free of attachment to the elongated tubular member in the expanded configuration, wherein at least one of the at least one barb is fixed to the at least one filament between and spaced away from adjacent junctions;
- wherein when in the collapsed configuration, the at least one filament is configured to exert a constraining force on the free first end to position the at least one barb radially inward of the at least one filament and when in the expanded configuration, the free first end of the at least one barb extends radially outward from the elongated tubular member.

20. The stent of claim 19, wherein the at least one barb comprises a shape memory material.

* * * * *